(12) United States Patent
Takagi et al.

(10) Patent No.: US 6,269,140 B1
(45) Date of Patent: *Jul. 31, 2001

(54) X-RAY COMPUTERIZED TOMOGRAPHY APPARATUS CONTROL METHOD THEREFOR AND IMAGE GENERATING METHOD USING THE APPARATUS

(75) Inventors: Hiroshi Takagi, Kashiwa; Hisashi Kobayashi, Tokyo, both of (JP)

(73) Assignee: Hitachi Medical Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/708,950

(22) Filed: Sep. 6, 1996

(30) Foreign Application Priority Data

Sep. 11, 1995 (JP) .................................................. 7-232300

(51) Int. Cl.[7] ........................................................ H05G 1/10
(52) U.S. Cl. .................................................. 378/8; 378/95
(58) Field of Search .......................................... 378/8, 95

(56) References Cited

U.S. PATENT DOCUMENTS

| | | | | |
|---|---|---|---|---|
| 3,952,201 | * | 4/1976 | Hounsfield | 378/8 |
| 4,086,492 | * | 4/1978 | Lodge | 378/17 |
| 4,530,109 | * | 7/1985 | Klausz | 378/8 |

* cited by examiner

Primary Examiner—Craig E. Church
(74) Attorney, Agent, or Firm—Antonelli, Terry, Stout & Kraus, LLP

(57) ABSTRACT

An X-ray computerized tomography apparatus which includes: an X-ray generating source for irradiating an object with X-rays; a unit for detecting X-rays transmitted through the object; a scan unit for controlling direction of irradiation with X-rays so that a periphery of the object is scanned in a predetermined direction with the X-rays from the X-ray generating source; and a control unit for controlling a scan speed of the scan unit on the basis of an external signal synchronized with movement of a part or whole of the object. An X-ray computerized tomography apparatus which includes: a rotary member on which an X-ray source and an X-ray detector are disposed so as to be opposite to each other with respect to a center of rotation of the rotary member; an opening portion provided so that an object can be arranged on the center of rotation of the rotary member; a scan control section for controlling drive of the X-ray source and the rotary member so that the rotary member rotates to thereby perform scan on the periphery of the object with the X-rays in a direction of a sliced face crossing a body axis of the object; an image reconstituting section for generating a slice image signal of the object on the basis of an output signal of the X-ray detector obtained during the scan; a display unit for displaying a slice image of the object on the basis of the slice image signal; and a scan speed control section for receiving an electrocardiogram signal of the object to thereby control a rotational speed of the rotary member on the basis of the electrocardiogram signal. An image generating method by using an X-ray computerized tomography apparatus, which includes the steps of: scanning an object with X-rays along a sliced face crossing a body axis of the object while an irradiation source of the X-rays is rotated around the object; changing relative positions of the object and the irradiating source along the direction of the body axis and repeating the step of scanning the object with the X-rays every time the relative positions are changed; receiving an electrocardiogram signal of the object and controlling a scan speed of the X-rays synchronously with a period of the electrocardiogram signal; detecting the X-rays transmitted through the object every time the scan is performed to thereby collect image information with respect to a sliced face of the object; and generating three-dimensional image information of the object on the basis of image information collected by scan on a plurality of different sliced faces.

19 Claims, 3 Drawing Sheets

X-RAY COMPUTERIZED TOMOGRAPHY APPARATUS CONTROL METHOD THEREFOR AND IMAGE GENERATING METHOD USING THE APPARATUS

BACKGROUND OF THE INVENTION

The present invention relates to X-ray computerized tomography (hereinafter abbreviated to "CT") apparatus, and particularly to an X-ray CT apparatus for use preferably for cardiac function diagnosis, a method for controlling the apparatus and a method for generating images by using the apparatus.

An X-ray CT apparatus is provided, as shown in FIG. 4, with a scanner gantry section 10 for performing radiation and detection of R-rays, a data processing section 20 for processing measurement data detected by the scanner gantry section 10 into a CT image signal, and a display unit 30 for displaying the CT image. The scanner gantry section 10 is provided with a rotary disc 11, an opening portion 14 formed in the rotary disc 11, an X-ray tube 12 mounted on the rotary disc 11, an X-ray detector 15 attached so as to face the X-ray tube 12, and a detector circuit 16 for converting an output signal of the X-ray detector 15 into a digital signal S1. The rotary disc 11 is designed so as to rotate around an object 18 laid down on a bed (not shown) disposed in the opening portion 14 while the X-rays are radiated onto one sliced section of the object 18. As a result of one scan, one slice image can be obtained by one scan. If such a scan is repeated by a plurality of times while the position of the rotary disc 11 relative to the object 18 is being changed, data of a plurality of images can be obtained with respect to a desired image pick-up portion. The rotation of the rotary disc 11 and the width of X-ray flux are controlled by a scanner gantry control circuit 17.

As the scan method for obtaining CT images, there are a full scan method in which one scan is completed by making an X-ray source rotate around an object by 360 degrees and a half scan method in which scan is completed by X-ray movement by about 210~240 degrees. In the full scan method, generally, image pick up is carried out in a time of one to several seconds per scan.

In the data processing section 20, on the other hand, a digital signal S1 is sent to a CT image operation section 21 from the detector circuit 16 at every scan. Operation such as arrangement processing, filtering processing, reverse projection processing, etc. are performed in the CT image operation section 21, so that image data are generated with respective to the sliced section. Attribute information relating to the images is added to the image data in an image information adding section 22. The image data are processed into a display signal in a display circuit section 24. Slice images are displayed on a display unit 30.

There is also such a CT apparatus in which a three-dimensional image generating section is provided (between the image information adding section 22 and the display circuit section 24) in the data processing section so that three-dimensional information is extracted from a series of CT images to thereby display three-dimensional CT images. In this case, data of a plurality of tomography images obtained by a plurality of scans are reconstituted into three-dimensional image data.

Two-dimensional sectional images in the direction of a body axis of the object crossing the sliced face in the scanning direction, such as sagittal images or coronal images, can be obtained in a manner in which only data components of a specific plane parallel with a body axis are extracted out of three-dimensional image data, and two-dimensional images of the plane are reconstructed on the basis of the extracted data components. Three-dimensional images can be obtained in a manner in which data components of specific three-dimensional coordinates are extracted out of three-dimensional image data, and three-dimensional images are reconstructed on the basis of the extracted data components.

The sagittal images, coronal images and three-dimensional tomography images can be obtained by means of computer graphics technique disclosed in the "Three Dimensional Processing For Computer Tomography Images" described in the magazine titled "PIXEL", Vol. 16, pp. 28–35, 1984, 1.

In a case of performing cardiac image-diagnosis by using such an X-ray CT apparatus, image distortion due to cardiac pulsation occurs in the CT images. Particularly in the case of a plurality of CT images which are different in measurement time from each other, the images are not coincident with each other in pulsation phase so that the image distortion increases in the three-dimensional images or in the reconstructed sagittal (or coronal) images to lose values of diagnosis. In order to avoid this disadvantage, there has been proposed a method (ECG gated CT image reconstituting method) in which image operation is carried out by collecting only data measured from the measurement data by a plurality of scans at a predetermined phase of the electrocardiographic complex. In this method, however, since only specific measurement data are used among a large number of measurement data, there is a disadvantage that image noise due to shortage of the quantity of data becomes large or the time for test and the quantity of use of a contrast medium increase because the number of scans is increased so as to make the SN ratio large.

In the conventional X-ray CT apparatus, the rotational speed of the rotary disc, that is, the scan speed has no connection with the period of the cardiac pulsation of a object and scan is performed at a constant speed. Accordingly, among a plurality of slice images which are different in measurement time from each other, the images are not coincident in phase of pulsation with each other so that distortion appears in cardiac sagittal or coronal images or cardiac three-dimensional images to make the diagnosis difficult.

SUMMARY OF THE INVENTION

It is therefore an object of the present invention to provide an X-ray CT apparatus in which slice images or three-dimensional images of a moving object can be reconstructed without any distortion and to provide a control method therefor.

It is another object of the present invention to provide an X-ray CT apparatus in which sagittal or coronal images, or three-dimensional images effective for diagnosis of a heart or any other organ can be clearly reconstructed without increasing the time taken for examination and the quantity of use of a contrast medium, and to provide a control method therefor.

It is a further object of the present invention to provide a method in which slice images or three-dimensional images of a object can be reconstructed by controlling the scan speed synchronously with an electrocardiogram of the object.

The X-ray CT apparatus, the control method therefor, and the image generating method according to the present invention commonly have a technical subject matter that an outside signal corresponding to movement of an object to be inspected or a living body is received from the outside of a scan controller and the scan speed is controlled synchronously with the outside signal.

According to an aspect of the present invention, an X-ray computerized tomography apparatus comprises: an X-ray generating source for irradiating an object with X-rays; means for detecting X-rays transmitted through the object; a scan means for controlling direction of irradiation with X-rays so that a periphery of the object is scanned in a predetermined direction with the X-rays from the X-ray generating source; and a control means for controlling a scan speed of the scan means on the basis of an external signal synchronized with movement of a part or whole of the object.

According to another aspect of the present invention, an X-ray computerized tomography apparatus comprises: a rotary member on which an X-ray source and an X-ray detector are disposed so as to be opposite to each other with respect to a center of rotation of the rotary member; an opening portion provided so that a object can be arranged on the center of rotation of the rotary member; a scan control section for controlling drive of the X-ray source and the rotary member so that the rotary member rotates to thereby perform scan on the periphery of the object with the X-rays in a direction of a sliced face crossing a body axis of the object; an image reconstituting section for generating a slice image signal of the object on the basis of an output signal of the X-ray detector obtained during the scan; a display unit for displaying a slice image of the object on the basis of the slice image signal; and a scan speed control section for receiving an electrocardiogram signal of the object to thereby control a rotational speed of the rotary member on the basis of the electrocardiogram signal.

According to a further aspect of the present invention, an image generating method by using an X-ray computerized tomography apparatus, comprises the steps of: scanning a object with X-rays along a sliced face crossing a body axis of the object while an irradiation source of the X-rays is rotated around the object; changing relative positions of the object and the irradiating source along the direction of the body axis and repeating the step of scanning the object with the X-rays every time the relative positions are changed; receiving an electrocardiogram signal of the object and controlling a scan speed of the X-rays synchronously with a period of the electrocardiogram signal; detecting the X-rays transmitted through the object every time the scan is performed to thereby collect image information with respect to a sliced face of the object; and generating three-dimensional image information of the object on the basis of image information collected by scan on a plurality of different sliced faces.

DESCRIPTION OF THE PREFERRED EMBODIMENTS

Referring to the accompanying drawings, the X-ray CT apparatus according to the present invention and the image generating method using the X-ray CT apparatus will be described below with respect to image reconstruction in the cardiac portion of a human body by way of example.

Figure 1:
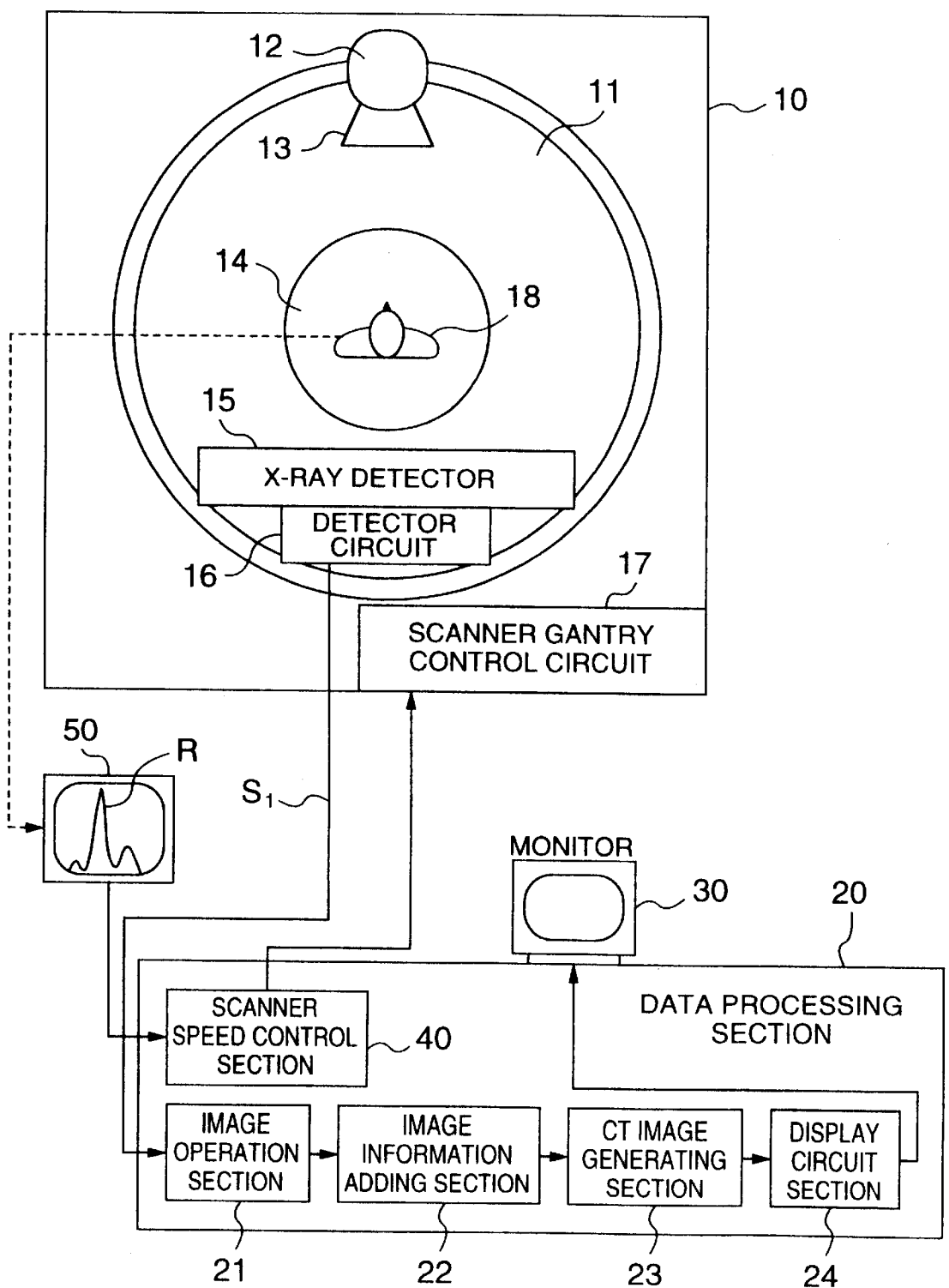
FIG. 1 is a view showing the configuration of an embodiment of the X-ray CT apparatus according to the present invention.

FIG. 1 is a view showing an embodiment of the X-ray CT apparatus according to the present invention. The X-ray CT apparatus is provided with a scanner gantry section 10 for performing radiation and detection of X-rays, rays, a data processing section 20 for processing measurement data detected by the scanner gantry section 10 into a CT image signal, and a display unit 30 for displaying the CT image. The scanner gantry section 10 is provided with a rotary disc 11, an X-ray tube 12 mounted on the rotary disc 11, a collimator 13 attached to the X-ray tube 12 for controlling the direction of X-ray beam, an opening portion 14 formed in the rotary disc 11, an X-ray detector 15 mounted on the rotary disc 11, a detector circuit 16 for converting an output signal of the X-ray detector 15 into a digital signal S1, and a scanner gantry control circuit 17 which is a scan control section for controlling the rotation of the rotary disc 11 and the width of the X-ray beam.

The data processing section 20 is provided with an image operation section 21 for performing CT image reconstruction on the basis of the data outputted from the measurement data detector circuit 16, an image information adding section 22, a CT image generating section 23 for forming three-dimensional image information from a series of tomographic image data, and a display circuit section 24 for adjusting the gain of display of a CT image signal.

The X-ray CT apparatus is further provided with a scan speed control section 40 supplied with an electrocardiographic complex from an electrocardiograph 50 for controlling the rotational speed of the rotary disc 11 on the basis of the electrocardiographic complex.

Figure 2:
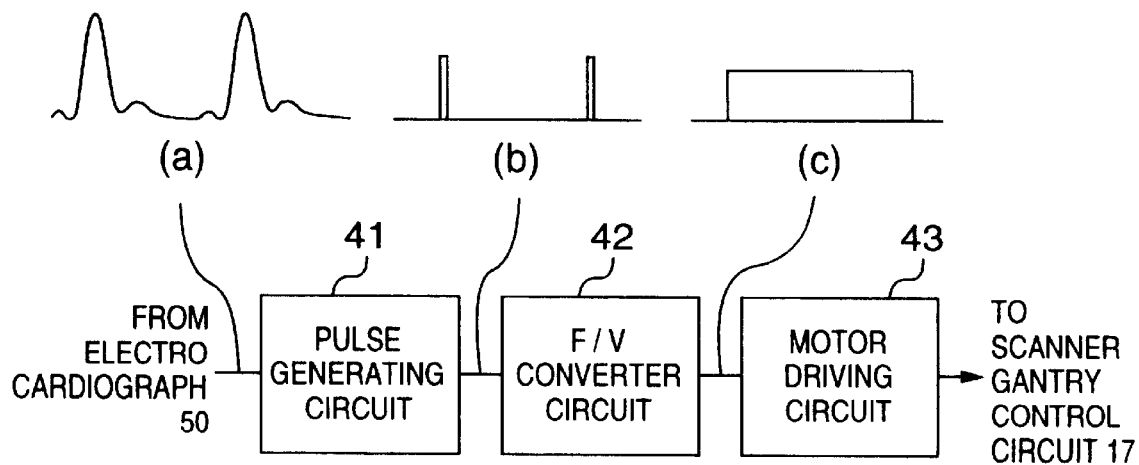
FIG. 2 is a block diagram showing a scan speed control section according to the present invention.

As shown with schematic configuration in FIG. 2, the scan speed control section 40 is constituted by a pulse generating circuit 41, a frequency-to-voltage (F/V) converter circuit 42, and a motor driving circuit 43 for controlling a rotary-disc driving motor (not-shown). In FIG. 2, waveforms (a), (b) and (c) show respectively an electrocardiographic complex supplied from the electrocardiograph 50, pulses outputted from the pulse generating circuit 41, and a control voltage outputted from the F/V converter circuit 42. The pulse generating circuit 41 outputs repetitive pulses corresponding to the period of the peaks, for example, R waves, of the electrocardiographic complex. The F/V converter circuit 42 generates a control voltage having an amplitude corresponding to the frequency of the pulses supplied from the pulse generating circuit 41. The motor driving circuit 43 controls the speed of the rotary disc driving motor (not shown) correspondingly to the control voltage supplied thereto. The F/V converter circuit 42 generates a control voltage having an amplitude directly proportional to the frequency of the electrocardiographic complex to thereby make the frequency of the rotary disc equal to the frequency of the electrocardiographic complex. Generally, because the human pulsations have personal errors in a range of from several tens per minute to about 100 per minute, the rotational speed of the rotary disc is controlled so as to be in a range of from about 0.7 sec. per rotation to about 2 sec. per rotation in accordance with the personal errors.

Scan is started at the phase of the first R wave of a electrocardiogram signal, and the scan for one sliced face is ended immediately before the phase of the next R wave. The position of the object 18 or the scanner gantry section 10 is slightly moved in the direction of the body axis, and scan for another sliced face is started at the phase of the next R wave. If such an operation is repeated while the sliced face is moved, data of tomographic images in a plurality of different sliced faces can be obtained. All these data of tomographic images in the sliced faces are data at the identical phase of cardiac pulsations.

In the X-ray CT apparatus having such a configuration, X-rays are radiated from the X-ray tube 12 onto a object 18 in a condition that the object 18 is laid down on a bed (not shown) which is provided in the opening portion 14 of the scanner gantry section 10. The X-rays are given directivity by the collimator 13 and are detected by the X-ray detector 15. At that time, the X-rays are detected while the rotary disc 11 is rotated around the object 18 to thereby change the X-ray irradiating direction. After one rotation of the rotary disc 11 (one scan), the scanner gantry section 10 is moved along the body axis of the object and scan is performed for another sliced face. By repeating this operation, a predetermined positional region of the object can be scanned by a plurality of times. At every scan, a detection signal is converted into a digital signal S1 in the detector circuit 16 and transmitted to the data processing section 20. At that time, since the period per rotation (per scan) of the rotary disc 11 is synchronized with the electrocardiograph period of the object, it is possible to always make the rotation start timing at every scan identical with the cardiac diastole or constrictor to thereby obtain signals at the respective scans under the same conditions of the cardiac pulsation.

After a plurality of sliced faces in a predetermined region including the cardiac region of the object are scanned synchronously with the phase of the R wave of the electrocardiogram, sliced faces in one and the same region are scanned synchronously with the phase of the electrocardiogram slightly delayed from the phase of the R wave. Thus, if the synchronizing phase of the electrocardiogram is shifted successively while one and the same region are scanned, the state of the cardiac pulsation can be reconstituted as an animation. Of course, the phase of the electrocardiogram to be synchronized with the scan can be set freely by a person who performs diagnosis. Generally, the period of cardiac pulsation is not always fixed accurately but it may change. In this embodiment, the scan speed can be controlled while continuously following the period of the cardiac pulsation.

The data processing section 20 receives the measurement data sent from the detector circuit 16, stores the data and performs pre-processing including correction of removing offset contained in the measurement data, log correction of correcting a logarithmic-functionally attenuating signal to make it have a linear characteristic, reference correction of correcting fine fluctuations in intensity of the X-ray source, calibration correction of correcting the reference point of the CT value, ring correction, etc. The data subjected to the pre-processing is transferred to the image operation section 21 so as to further be subjected to processing for image reconstruction including arrangement processing to convert the projection data of radially radiated X-rays into projection data of parallel radiation, filtering processing, and back projection processing for reproducing an initial object by projection images from various directions. The data subjected to the processing for the image reconstruction is sent to the CT image generating section 23.

Figure 3:
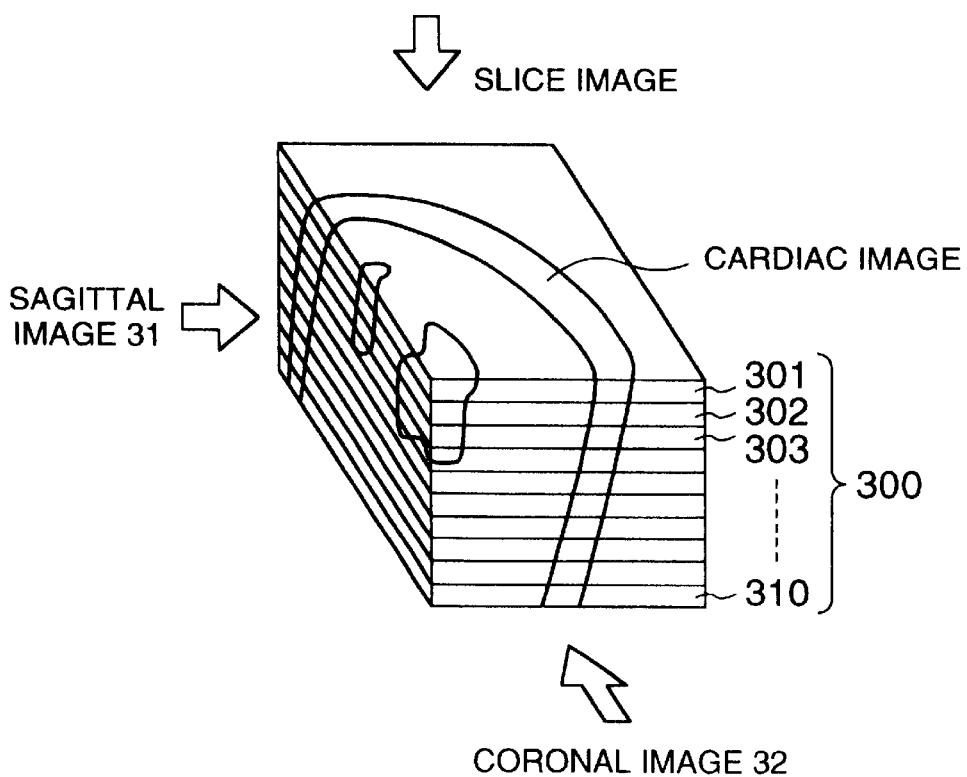
FIG. 3 is a view showing a method for obtaining a three-dimensional image or a vertical sectional image according to the present invention.
Figure 4:
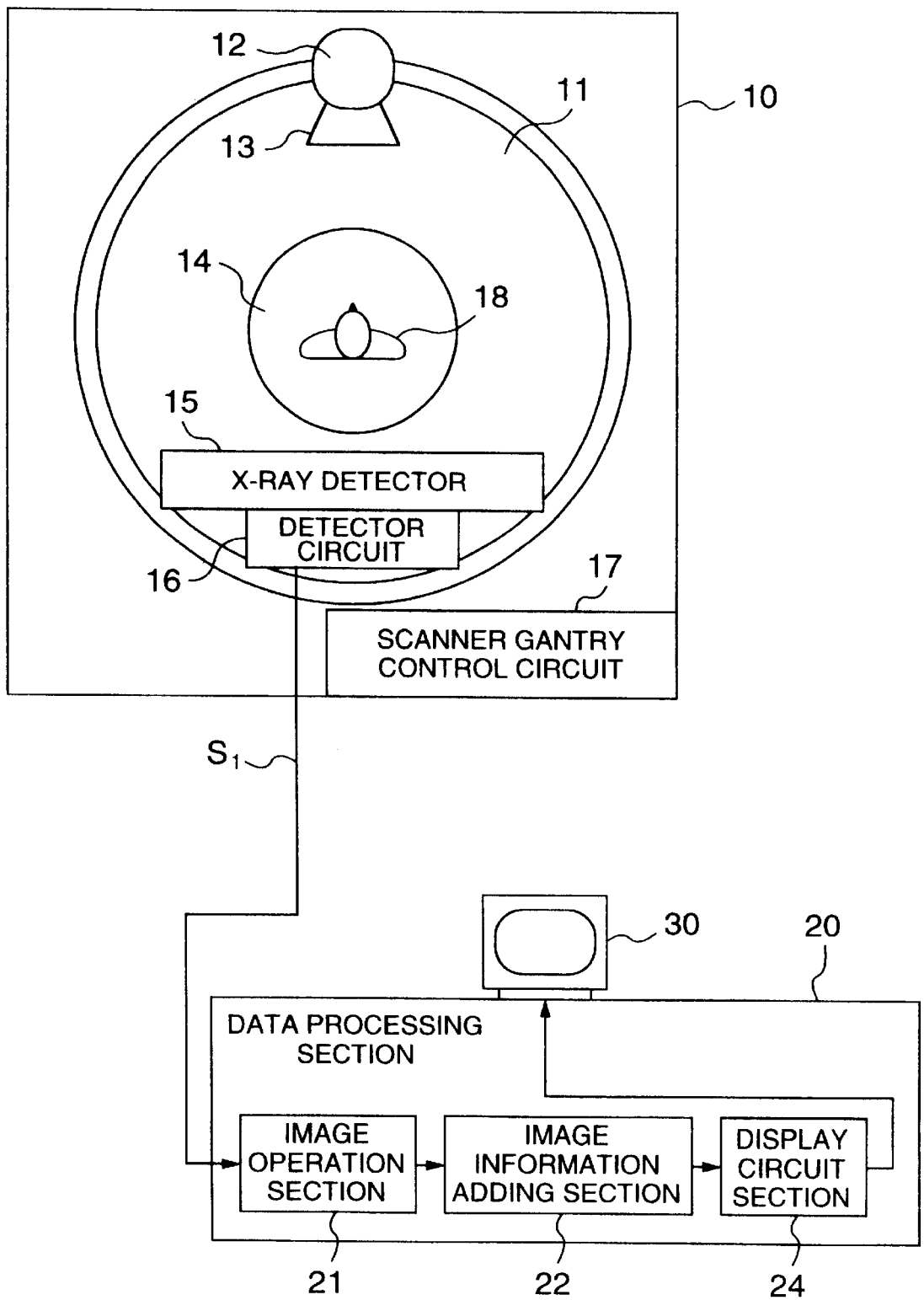
FIG. 4 is a view showing the configuration of a conventional X-ray CT apparatus.

The data to be sent to the CT image generating section 23 is constituted by a series 300 of several scan sets composed of two-dimensional data (cross-sectional data) 301~310 at the respective sliced faces of respective scans as shown in FIG. 3. The CT image generating section 23 extracts three-dimensional information from the series 300 and performs image processing for three-dimensional display, new sectional image display, or a combination thereof. To carry out such three-dimensional processing, there are various methods. For example, in the case of reconstitution of sectional images other than cross-sectional images, a large number of aforementioned cross-sectional data piled up in the direction of scan are reconstituted as tomographic images of other sections, for example, such as sagittal faces 31, or coronal faces 32. At that time, data between sections are interpolated if necessary. Further, for example, in the case of three-dimensional display of a cardiac surface or the like, first, region extraction is performed by threshold processing with respect to the respective two-dimensional data to draw border lines. In the case where it is difficult to obtain the border lines only by the threshold processing, the border lines are traced and inputted manually. Next, the border lines between adjacent sections are connected to each other. To perform the connection, if necessary, a known method such as a method in which data between sections are interpolated in accordance with necessity to form voxel data, or a triangular-element constituting method is employed. Next, necessary shading is applied to obtain a surface display image. Further, it is possible to combine this surface display image with the aforementioned sectional image.

The image signal formed thus in the CT image generating section 23 is subjected to gain-adjustment in the display circuit 24 and then supplied to the display unit 30 on which a reconstituted sectional image, a surface display image, a combined image of those sectional and surface display images, or the like, is displayed. In any case mentioned above, since the respective sectional data of FIG. 3 are data formed by using signals picked up under the same condition of the cardiac period, it is possible to suppress, as less as possible, the increase of image distortion due to discordance in phase of pulsation to thereby obtain a three-dimensional image and a sagittal (coronal) reconstituted image which are high in the values of diagnosis.

Though the case where the rotary disc rotates its one rotation (360 degrees) for one scan has been described in the above embodiment, the present invention can be applied to a so-called half scan method in which scan is carried out by the movement of the X-ray source by 210~240 degrees. Further, though description has been made above with respect to the X-ray CT apparatus in which the X-ray source mounted on the rotary disc is rotated to perform scan, the image generating method according to the present invention is applicable to an X-ray CT apparatus of a system in which scan is controlled by an electron beam.

As apparent from the above description, according to the X-ray CT apparatus of the present invention, a scan speed control function for controlling the rotational speed of a rotary disc with an X-ray source mounted thereon on the basis of an input from an electro-cardiograph is added to a scan control section for controlling the rotary disc, so that it is possible to establish a synchronizing relation of phase between the CT scan (rotation of the rotary disc) and the cardiac pulsation to thereby obtain a plurality of CT images corresponding to one and the same phase of pulsation. Further, according to the image generating method of the present invention, since a three-dimensional image or a sagittal (coronal) reconstituted image is formed from a plurality of CT images obtained by scan synchronously with the period of the electrocardiographic complex, it is possible to obtain a three-dimensional image which is remarkably improved in image distortion.

The X-ray CT apparatus, the control method therefor, and the image generating method according to the present invention are not limited to use for reconstruction of images of a cardiac region of a living body. The present invention can be used for reconstruction of images of regions of moving organs other than a heart. For example, in order to obtain CT images of a lung, a device for outputting a signal indicating a breath period of the lung is provided in place of the electrocardiograph 50, and the X-ray scan speed in the lung region is controlled synchronously with the breath period of the lung to thereby obtain a clear CT images of the lung without any distortion. Further, the present invention can be used for examination of an object having an element which is disposed inside the object and which performs periodic and repetitive movement. In that case, the object to be examined is put in the position of the object in FIG. 1 and, for example, a pressure sensor which detects the movement of the moving element and which outputs a detection signal may be used in place of the electrocardiograph 50. If the object is scanned synchronously with the period of the specific phase of the sensor signal, CT images with the moving element standing still at a certain phase can be reconstituted with no distortion.

What is claimed is:

1. An x-ray computerized tomography apparatus comprising:
    a cyclic movement detector detecting a cyclic movement of a living body to be examined and producing an output signal representing the cyclic movement of a part of said living body;
    an x-ray source irradiating said living body with x-rays;
    an x-ray detector detecting ones of said x-rays transmitted through said living body to obtain scan data with respect to multiple slices of said living body;
    a rotational member supporting said x-ray source and said x-ray detector on said rotational member on opposite sides of said living body and rotating around said living body;
    a driving mechanism driving a rotation of said rotational member;
    a slice position changing unit for changing a scanning position on said living body; and
    a control unit controlling a rotational speed of said rotational member in accordance with said output signal of said cyclic movement detector so that said x-ray detector collects the scan data necessary for complete reconstruction of a CT image for each slice of said living body within a single cycle of said cyclic movement of the part of said living body, and controlling said slice position changing unit and said driving mechanism to start scanning on different slices of said living body at substantially a same phase within different cycles of said cyclic movement of said part of said living body.

2. An apparatus according to claim 1, wherein said control unit more specifically, substantially synchronizes a frequency of rotation of said rotational member with a frequency of said cyclic movement detected by said cyclic movement detector.

3. An apparatus according to claim 1, wherein said control unit collects a scan data in a scan angle of 360 degrees within a single cycle of movement of said part of said living body.

4. An apparatus according to claim 1, wherein said control unit collects a scan data in a range of a 210 to 240 degrees scan angle within a single cycle of movement of said part of said living body.

5. An apparatus according to claim 1, wherein said driving mechanism changes a relative position between said object and said x-ray source in a direction perpendicular to a scanning direction of the x-rays, and said living body is scanned with x-rays from the x-ray source along with the scanning direction at each time when the relative position between said living body and said x-ray source is changed so as to obtain said scan data of said multiple slices.

6. An apparatus according to claim 1, wherein said cyclic movement detector collects the information about an electrocardiogram signal of a heart of said living body while said heart is scanned with the x-rays.

7. An apparatus according to claim 1, wherein said part of said living body is more specifically a living organism, and wherein said cyclic movement is a periodic metabolic movement within said living body.

8. An apparatus according to claim 7, wherein said periodic metabolic movement within said living body is more specifically one of a heart beating pulsation and breathing pulsation of said living body.

9. An x-ray computerized tomography method comprising the steps of:
    detecting a cyclic movement of a part of a living body to be examined;
    irradiating said living body with x-rays from an x-ray source disposed on a rotational member;
    rotating said rotational member around said living body;
    changing a slice position on said living body;
    detecting ones of said x-rays transmitted through said living body to obtain scan data with respect to multiple slices of said living body; and
    controlling a rotational speed of said rotational member in accordance with said cyclic movement of a part of said living body so as to collect the scan data necessary for complete reconstruction of a CT image for each slice of said living body within a single cycle of said cyclic movement of the part of said living body, and controlling said slice position and said rotational member to start scanning on different slices of said living body at substantially a same phase within different cycles of said cyclic movement of said part of said living body.

10. A method according to claim 9, further comprising a further step of reconstructing two or three dimensional image of a slice of living body on a basis of the collected scan data with respect to the multiple slices.

11. A method according to claim 10, wherein said controlling step substantially synchronizes a frequency of rotation of said rotational member with a frequency of the detected cyclic movement of said living body.

12. A method according to claim 10, wherein said reconstructing step includes a further step of controlling the collecting of said scan data with respect to each substantially complete slice of said living body within a single cycle of said cyclic movement of said part of said living body.

13. A method according to claim 10, wherein said step of controlling rotational speed is further adapted for controlling a rotational speed of said rotational member in accordance with said detected cyclic movement of the part of said living body, to allow said scan data with respect to each substantially complete slice of said living body within a single respective 360 degrees rotation of said rotational member.

14. A method according claim 10, wherein said step of changing scanning position includes further steps of changing a relative position between said living body and said x-ray source in a direction perpendicular to a scanning direction of the x-rays, and scanning said living body with x-rays from said x-ray source along with the scanning direction at each time when the relative position between said living body and said x-ray source is changed, so as to obtain the scan data with respect to said multiple slices.

15. A method according to claim 10, wherein said step of detecting a cyclic movement includes a further step of collecting the information about an electrocardiogram signal of a heart of said living body while said heart is scanned with the x-rays.

16. A method according to claim 10, wherein said part of said living body is more specifically a living organism, and said cyclic movement is metabolic movement within said living body.

17. A method according to claim 16, wherein said periodic metabolic movement within said living body is one of a heart beating pulsation and breathing pulsation of said living organism.

18. An x-ray computerized tomography (CT) apparatus comprising: a cyclic movement detector detecting a cyclic movement of a living body to be examined and producing an output signal representing the cyclic movement of a part of said living body;

an x-ray source irradiating said living body with x-rays;

an x-ray detector detecting ones of said x-rays transmitted through said living body to obtain scan data;

a rotational member supporting said x-ray source and said x-ray detector on said rotational member on opposite sides of said living body and rotating around said living body;

a driving mechanism driving a rotation of said rotational member; and a control unit controlling a rotational speed of said rotational member in accordance with said output signal of said cyclic movement detector so that said x-ray detector collects the scan data necessary for complete reconstruction of a CT image for a slice of said living body within a single cycle of said cyclic movement of the part of living body, and controlling the collecting of the scan data for differing slices of said living body to start at a substantially same phase within differing cycles of said cyclic movement of said part of said living body.

19. An apparatus according to claim 18, wherein said driving mechanism changes a relative position between said living body and said x-ray source in a direction perpendicular to a scanning direction of the x-rays, and scans said living body with x-rays from said x-ray source along with the scanning direction at each time when the relative position between said living body and said x-ray source is changed, so as to obtain the scan data with respect to multiple slices.

\* \* \* \* \*